US012087540B2

(12) United States Patent
Ryu et al.

(10) Patent No.: US 12,087,540 B2
(45) Date of Patent: Sep. 10, 2024

(54) FIELD EMISSION-TYPE TOMOSYNTHESIS SYSTEM, EMITTER FOR FIELD EMISSION-TYPE TOMOSYNTHESIS SYSTEM, AND METHOD OF MANUFACTURING EMITTER

(71) Applicant: CAT BEAM TECH CO., LTD., Seoul (KR)

(72) Inventors: Jehwang Ryu, Seoul (KR); Seung Jun Yeo, Seoul (KR); Jong Min Lim, Seoul (KR); Woo Seob Kim, Seoul (KR); Jeung Sun Ahn, Seoul (KR); Moonkyoo Kong, Seoul (KR); Jae Ik Jung, Seoul (KR); Jun Young Park, Seoul (KR)

(73) Assignee: CAT BEAM TECH CO., LTD., Seoul (KR)

( * ) Notice: Subject to any disclaimer, the term of this patent is extended or adjusted under 35 U.S.C. 154(b) by 455 days.

(21) Appl. No.: 17/297,215

(22) PCT Filed: Nov. 27, 2019

(86) PCT No.: PCT/KR2019/016427
§ 371 (c)(1),
(2) Date: May 26, 2021

(87) PCT Pub. No.: WO2020/111755
PCT Pub. Date: Jun. 4, 2020

(65) Prior Publication Data
US 2022/0028644 A1 Jan. 27, 2022

(30) Foreign Application Priority Data

Nov. 27, 2018 (KR) .................. 10-2018-0148994
Nov. 27, 2018 (KR) .................. 10-2018-0149004

(51) Int. Cl.
*H01J 1/304* (2006.01)
*H01J 35/06* (2006.01)
*H01J 35/10* (2006.01)

(52) U.S. Cl.
CPC ............ *H01J 1/304* (2013.01); *H01J 35/065* (2013.01); *H01J 35/10* (2013.01); *H01J 2201/30469* (2013.01); *H01J 2235/1033* (2013.01)

(58) Field of Classification Search
None
See application file for complete search history.

(56) References Cited

U.S. PATENT DOCUMENTS

| 5,438,605 | A | * | 8/1995 | Burke | ................ H01J 35/02 378/123 |
| 2003/0102222 | A1 | * | 6/2003 | Zhou | ................ B82Y 30/00 205/67 |

(Continued)

FOREIGN PATENT DOCUMENTS

| JP | 07-201489 A | 8/1995 |
| JP | 2005-516343 A | 6/2005 |

(Continued)

OTHER PUBLICATIONS

Korea Intellectual Property Office Notification of Reason for Refusal for KR 10-2018-0148994 dated Nov. 15, 2019.

(Continued)

*Primary Examiner* — Marcus H Taningco
(74) *Attorney, Agent, or Firm* — Sughrue Mion, PLLC

(57) ABSTRACT

Disclosed is a field emission-type tomosynthesis system including a vacuum body having a space therein; a plurality of sources provided inside the body, wherein each of the sources emits a plurality of electrons; and a plurality of anodes disposed inside the body to face the sources and responsible for emitting a plurality of X-rays, wherein each (Continued)

of the anodes faces a corresponding source among the sources, and the electrons collide with each of the anodes to generate X-rays, wherein the X-ray emission angle of each of the anodes is capable of being independently adjusted so as to focus the X-rays emitted toward an object located outside the body. With this configuration, a plurality of X-rays is focused on an object and is emitted to the object to obtain information, and the information is synthesized, thereby improving the reliability of information about the object.

19 Claims, 20 Drawing Sheets

(56) References Cited

U.S. PATENT DOCUMENTS

| | | | |
|---|---|---|---|
| 2003/0185985 A1 | 10/2003 | Bronikowski et al. | |
| 2008/0074026 A1* | 3/2008 | Sakai | H01J 1/304 |
| | | | 313/309 |
| 2011/0051895 A1* | 3/2011 | Vogtmeier | A61B 6/4021 |
| | | | 378/92 |
| 2012/0300901 A1* | 11/2012 | Lewalter | H01J 35/13 |
| | | | 378/126 |
| 2020/0305809 A1* | 10/2020 | Schwoebel | H01J 35/147 |
| 2021/0239629 A1* | 8/2021 | Chuang | H01J 35/066 |

FOREIGN PATENT DOCUMENTS

| | | |
|---|---|---|
| JP | 2007-012619 A | 1/2007 |
| JP | 2013-504365 A | 2/2013 |
| KR | 10-2005-0001090 A | 1/2005 |
| KR | 10-2006-0080728 A | 7/2006 |
| KR | 10-2009-0084189 A | 8/2009 |
| KR | 10-2011-0075726 A | 7/2011 |
| KR | 10-1227353 B1 | 1/2013 |
| KR | 10-1266618 B1 | 5/2013 |
| KR | 10-2016-0084835 A | 7/2016 |
| WO | 2009/021015 A2 | 2/2009 |

OTHER PUBLICATIONS

Korea Intellectual Property Office Grant of Patent for KR 10-2018-0149004 dated Jul. 14, 2020.
Korea Intellectual Property Office Grant of Patent for KR 10-2020-0091045 dated Sep. 21, 2020.
International Search Report for PCT/KR2019/016427 dated Mar. 4, 2020 [PCT/ISA/210].

* cited by examiner

[FIG. 1]
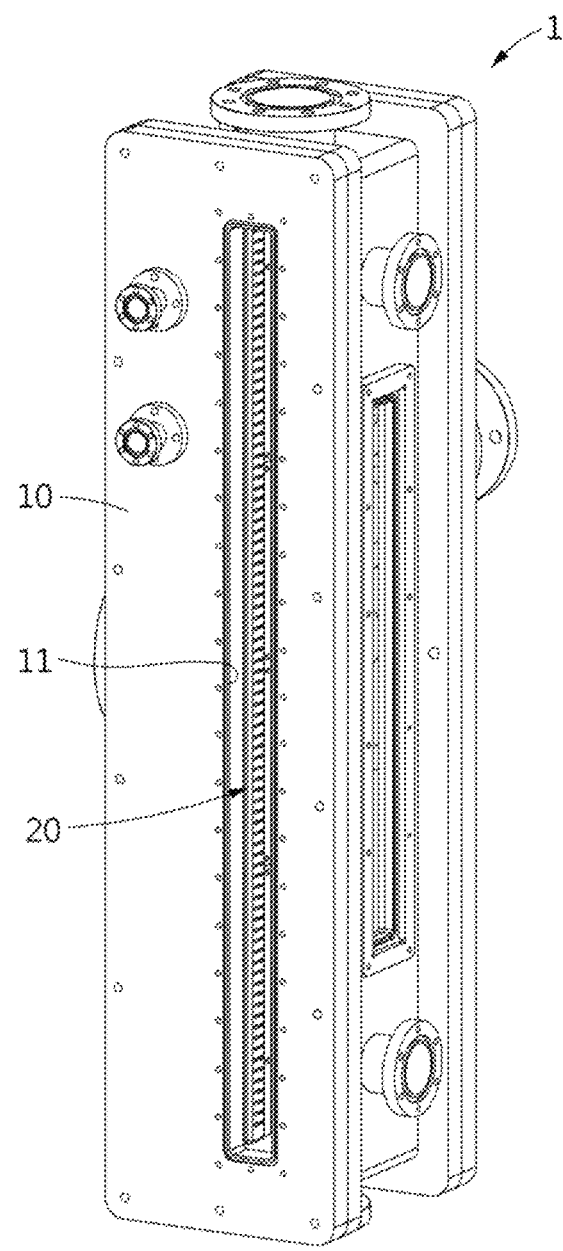

[FIG. 2]
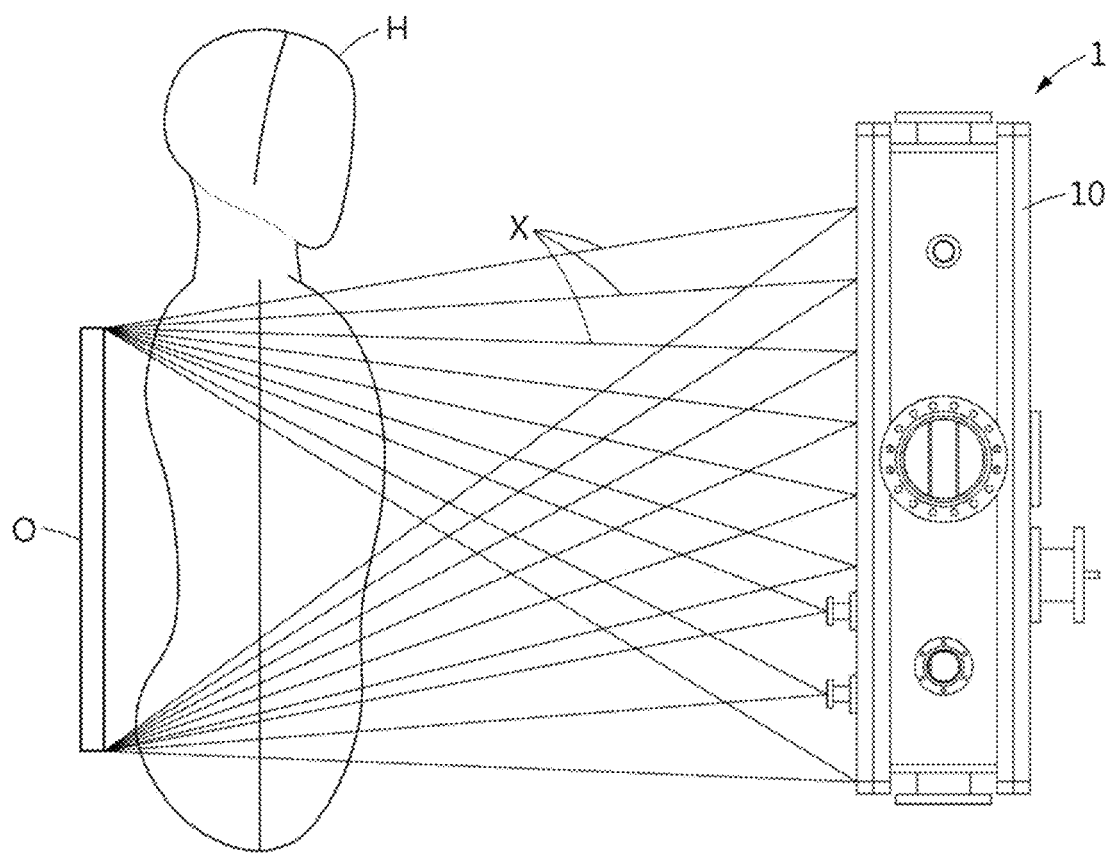

[FIG. 3]
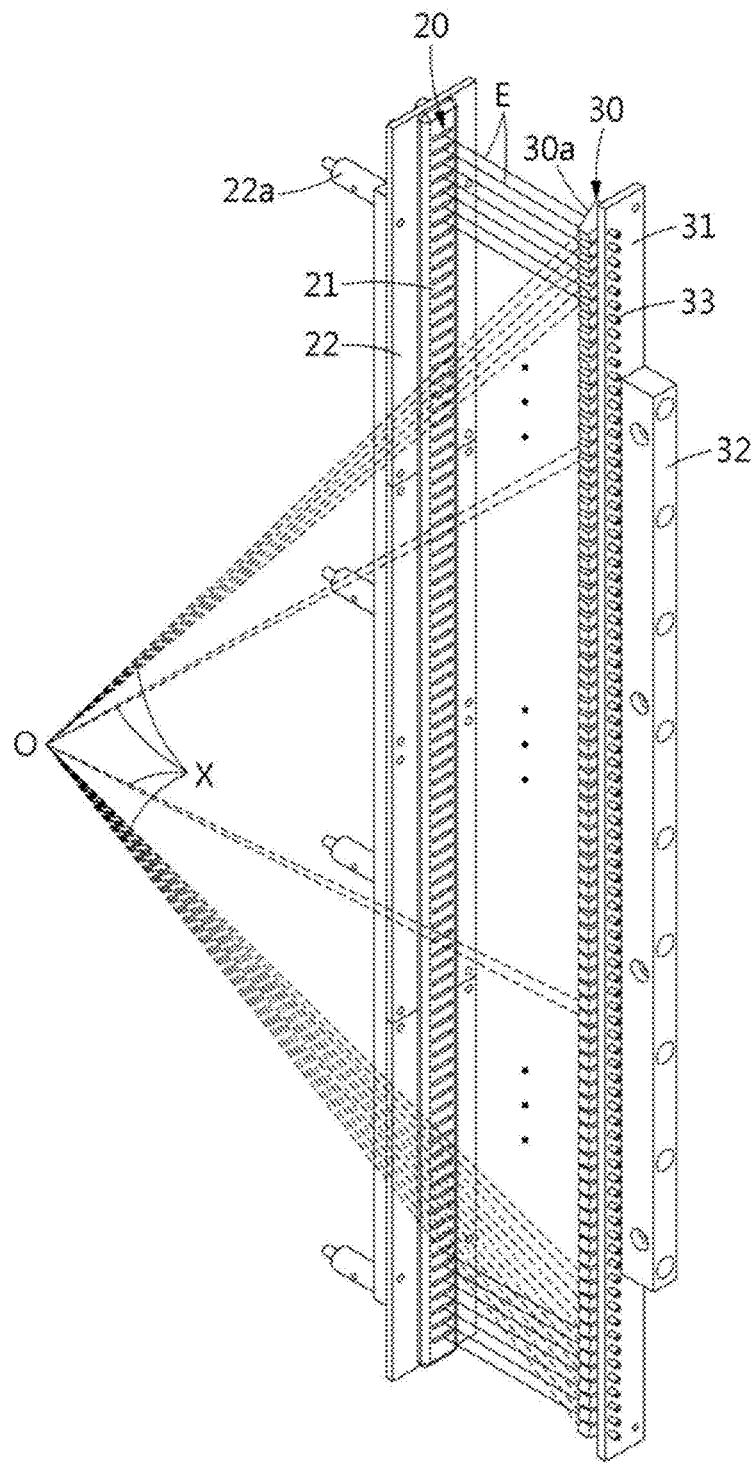

[FIG. 4]
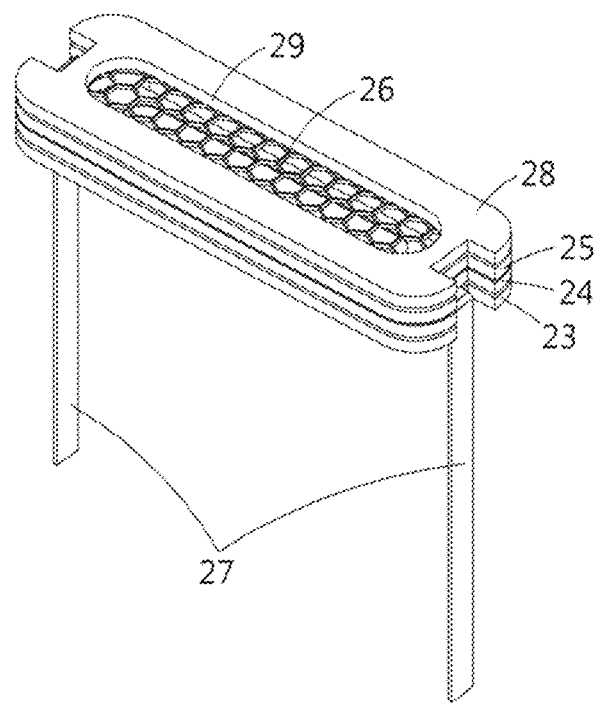

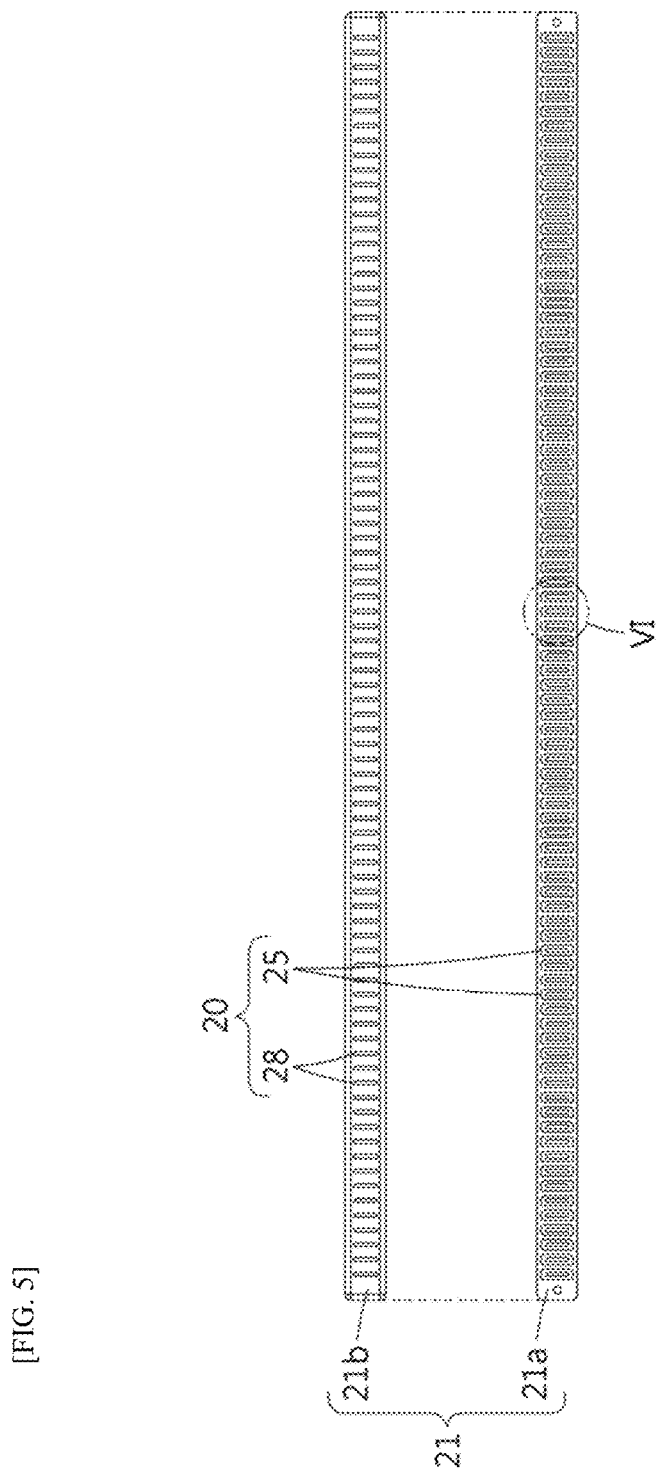

[FIG. 6]
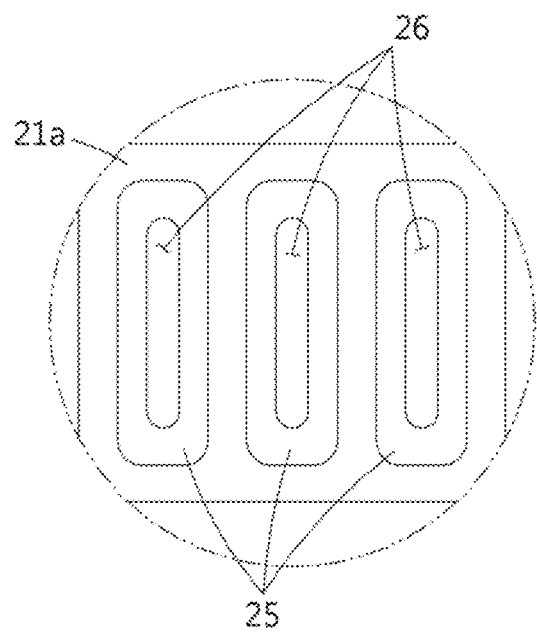

[FIG. 7]
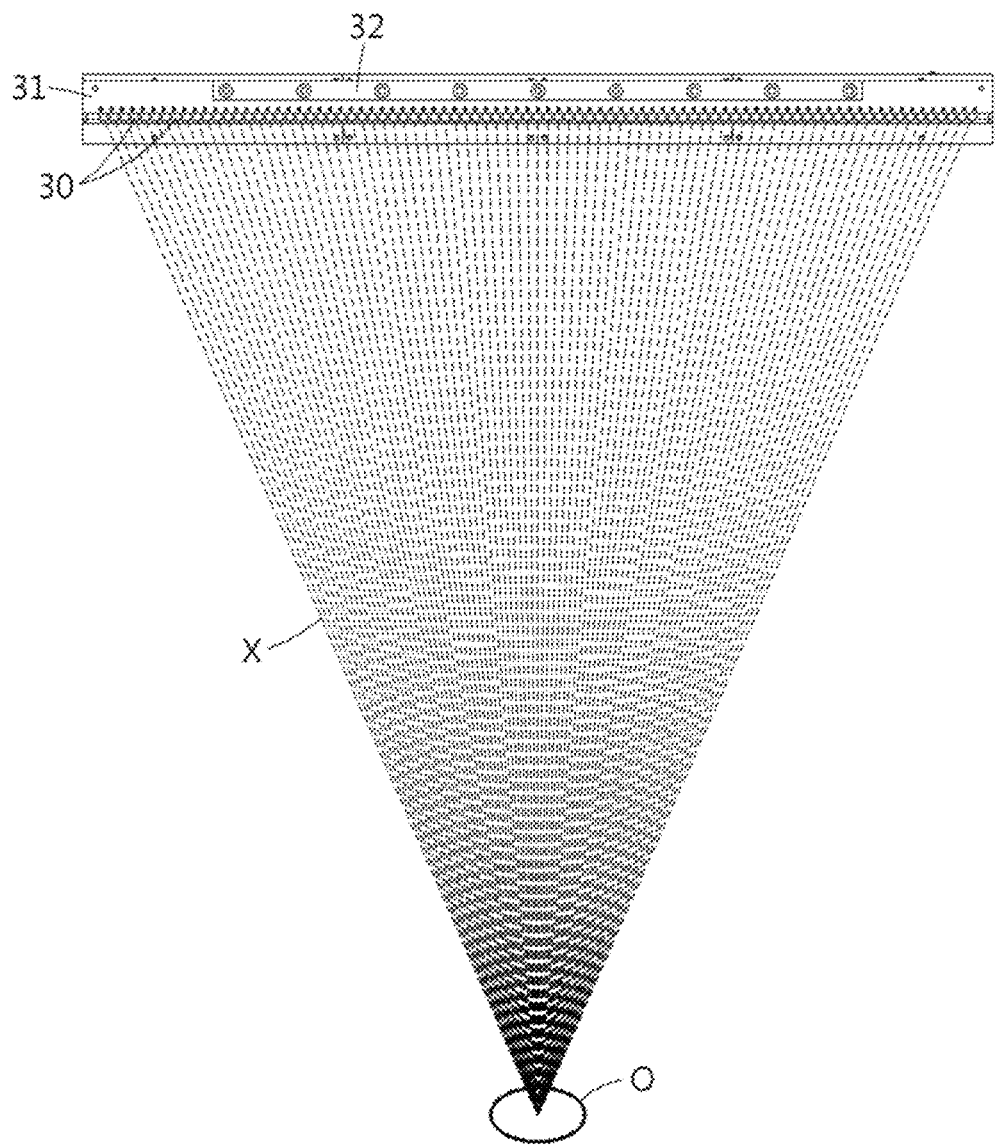

[FIG. 8]
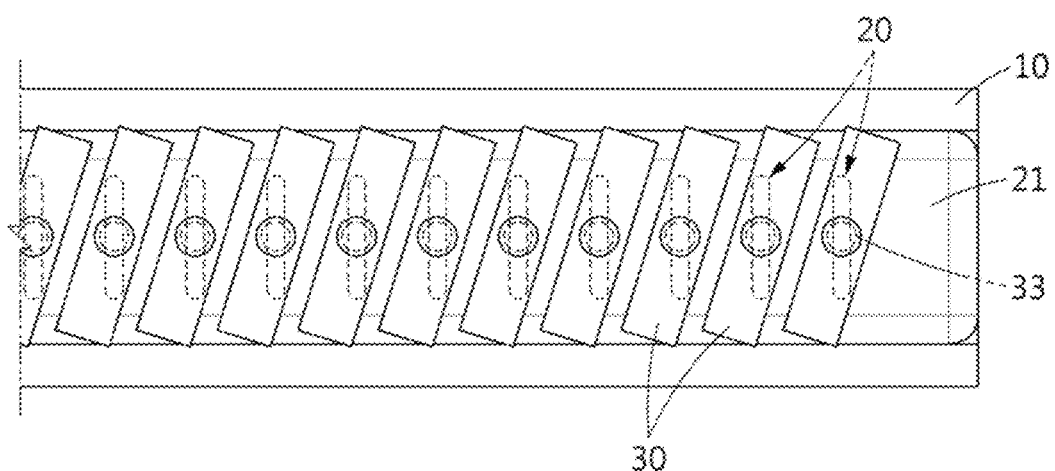
[FIG. 9]
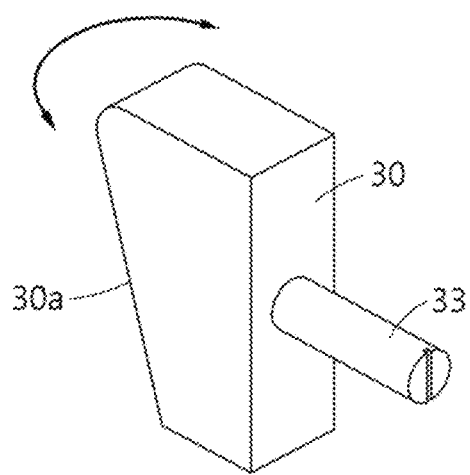

[FIG. 10]
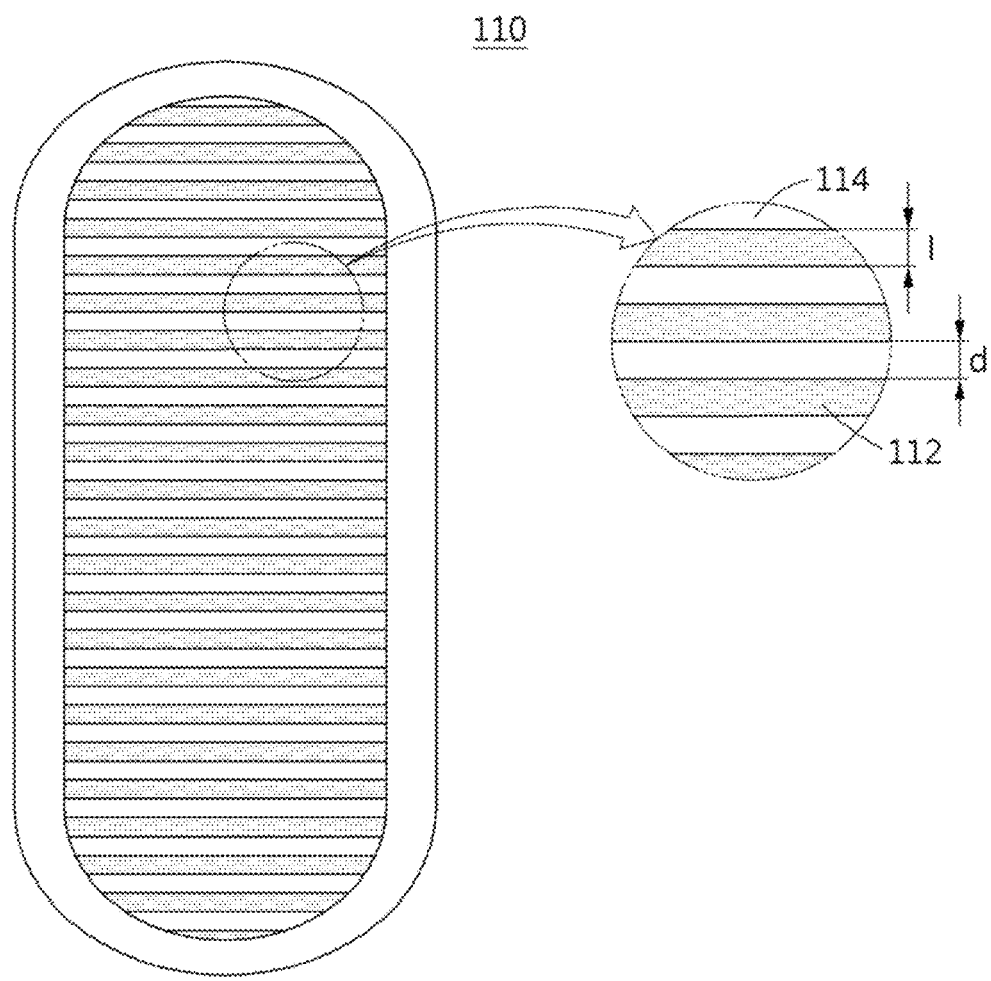

[FIG. 11A]
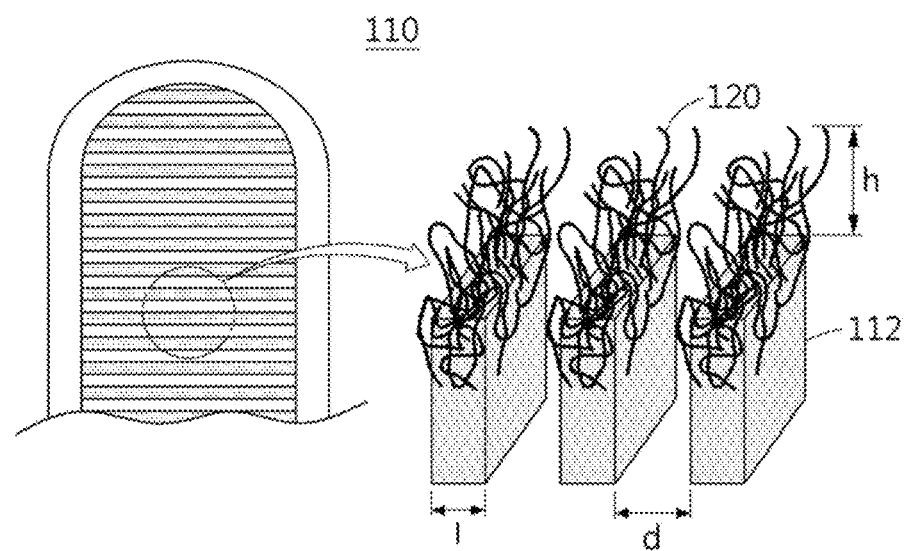
[FIG. 11B]
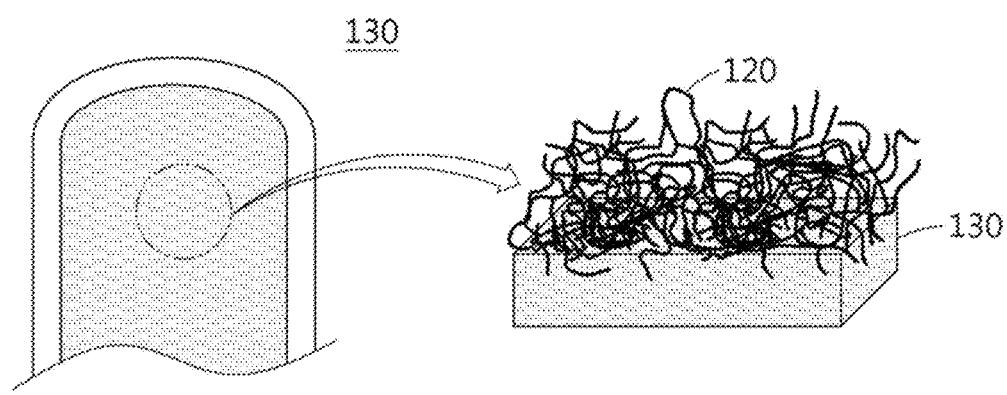

[FIG. 12]
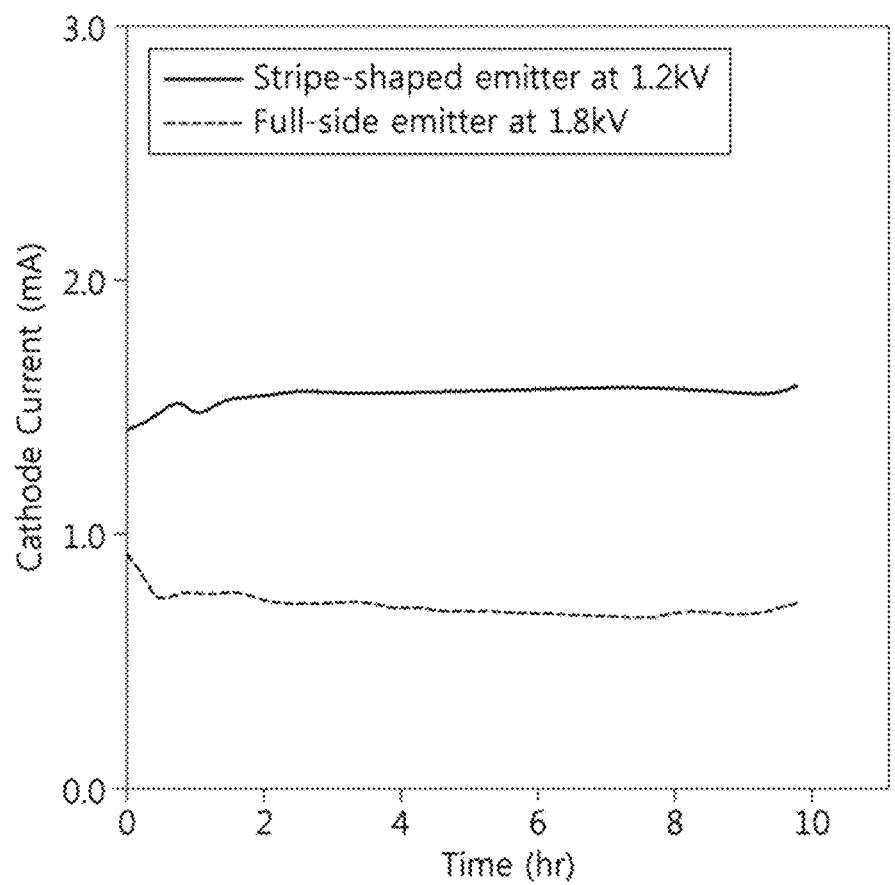

[FIG. 13]
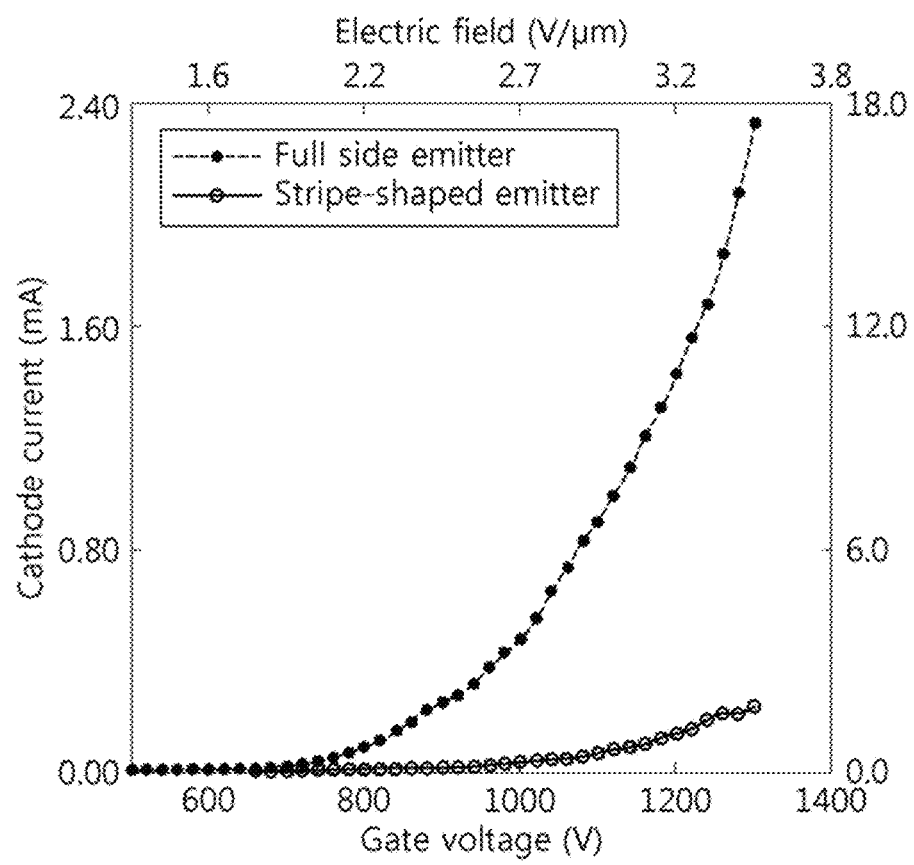

[FIG. 14]
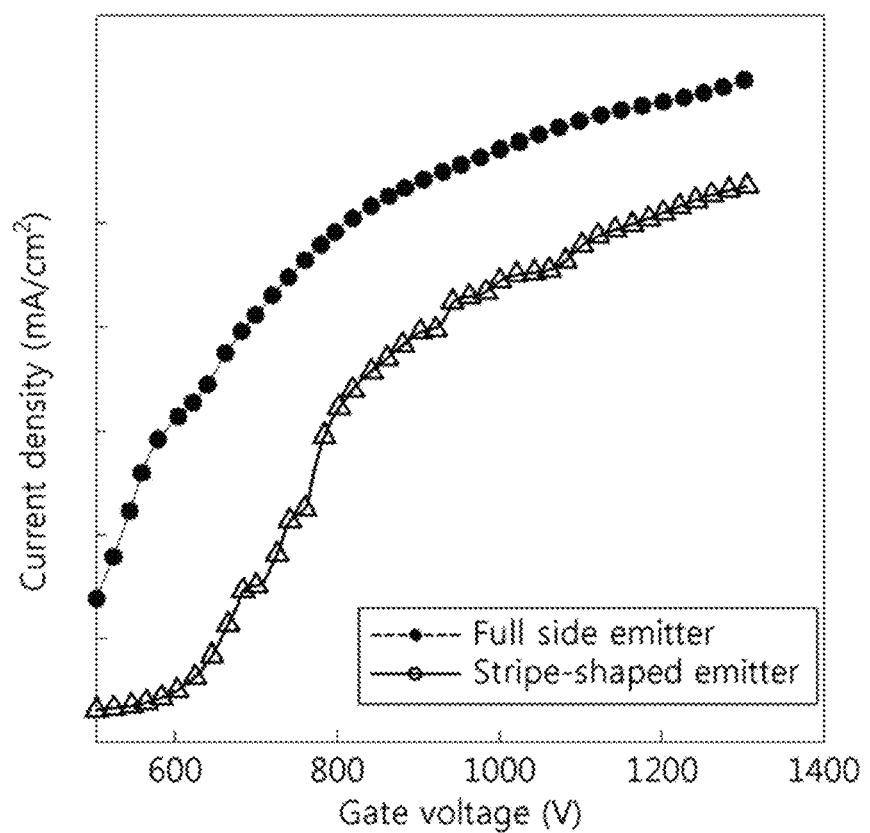

[FIG. 15]
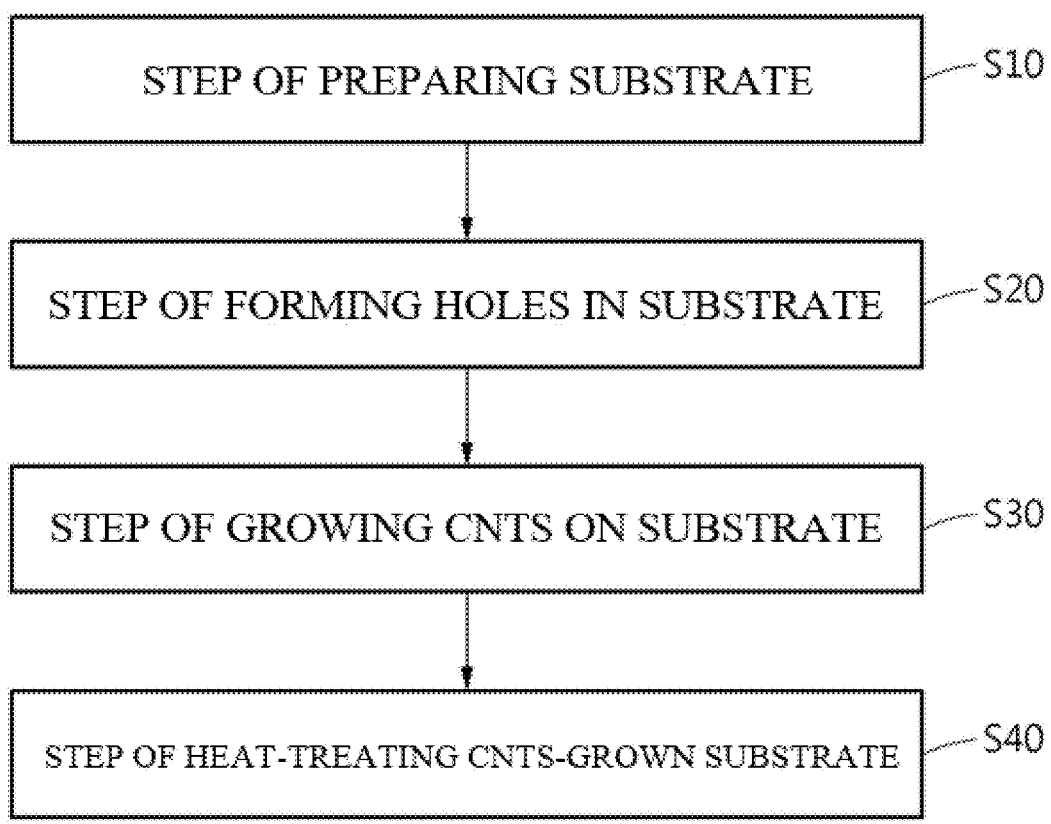

[FIG. 16]
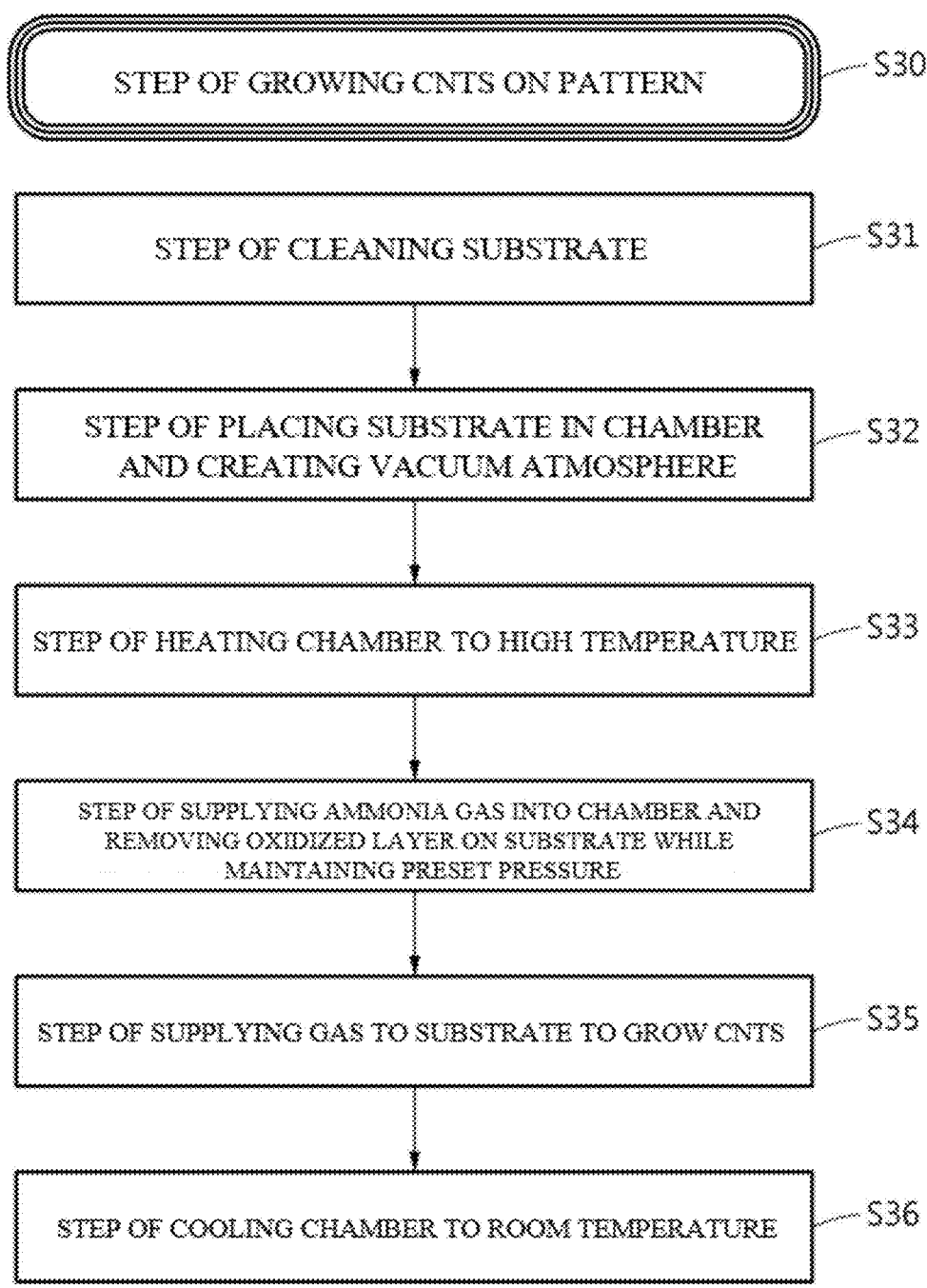

[FIG. 17A]
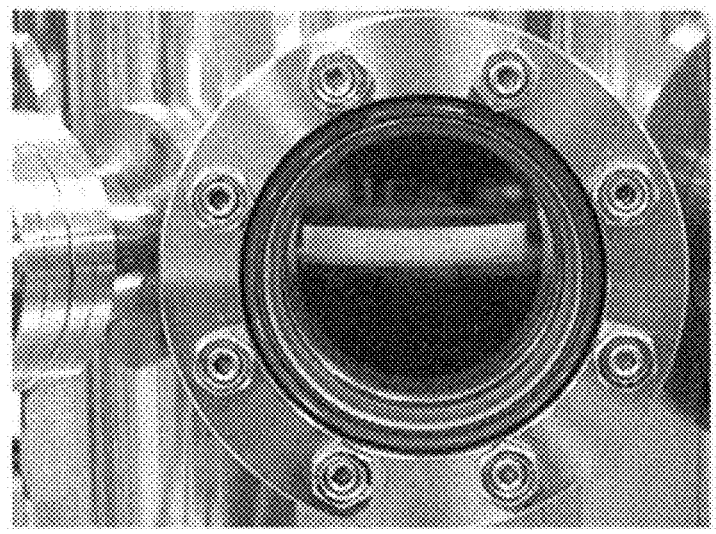
[FIG. 17B]
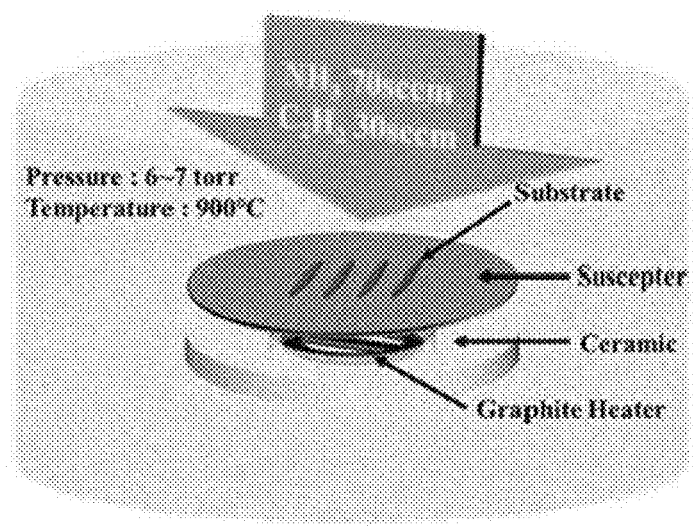

[FIG. 17C]
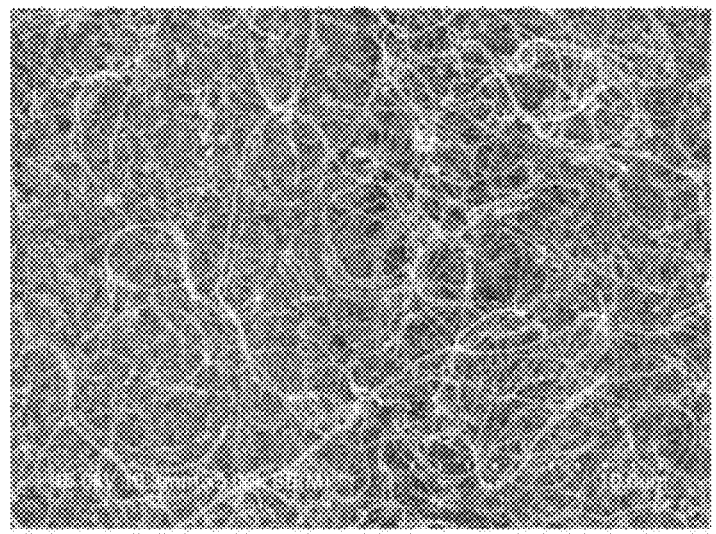
[FIG. 17D]
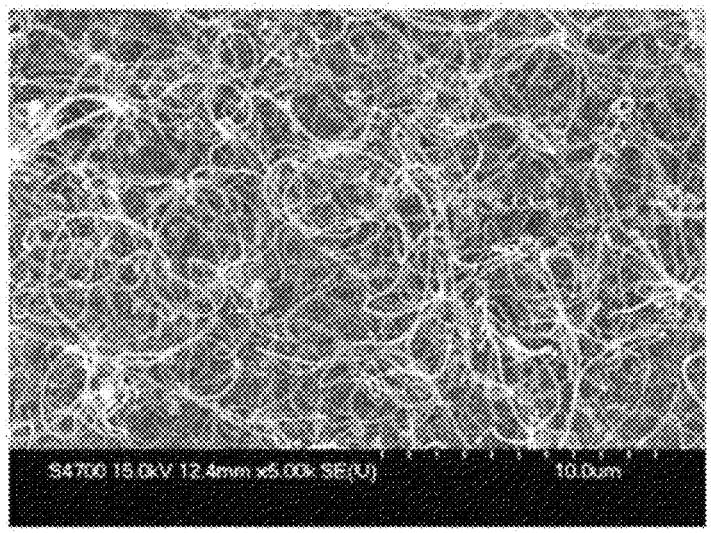

[FIG. 18]
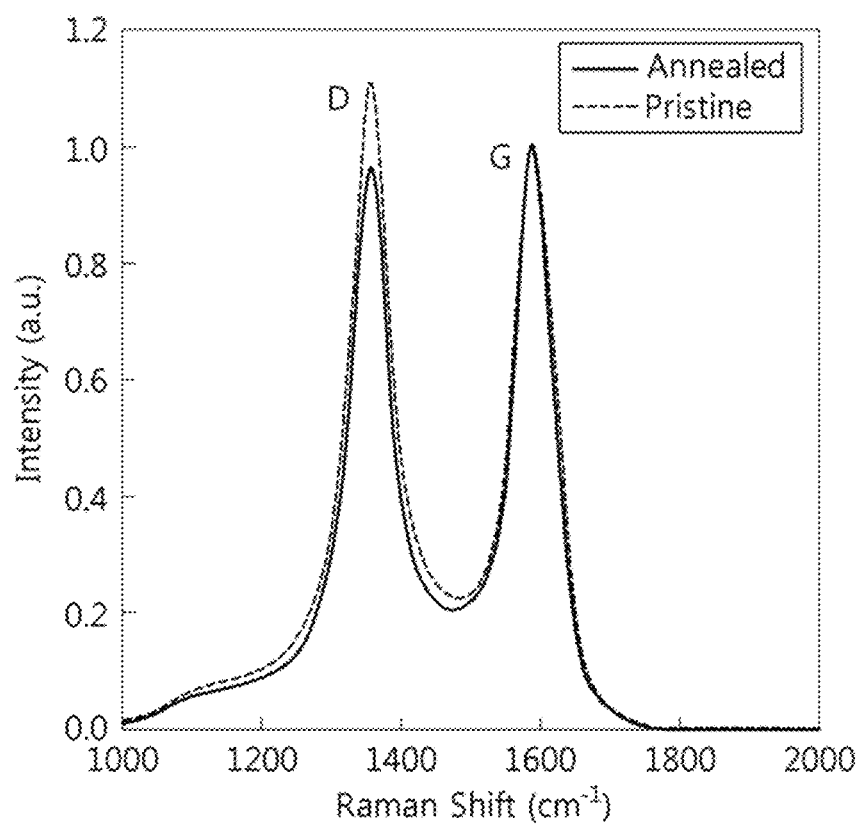

[FIG. 19]
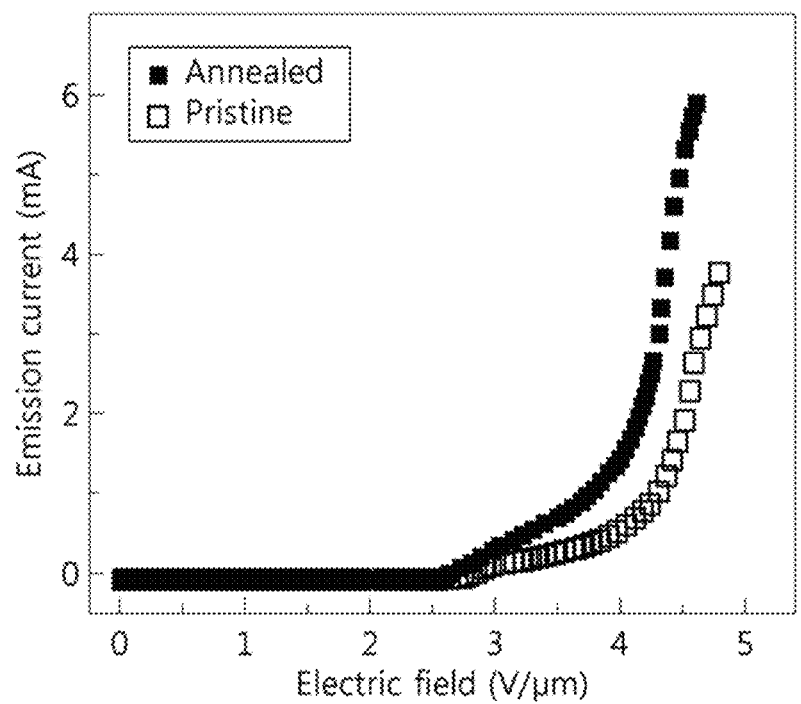

[FIG. 20]
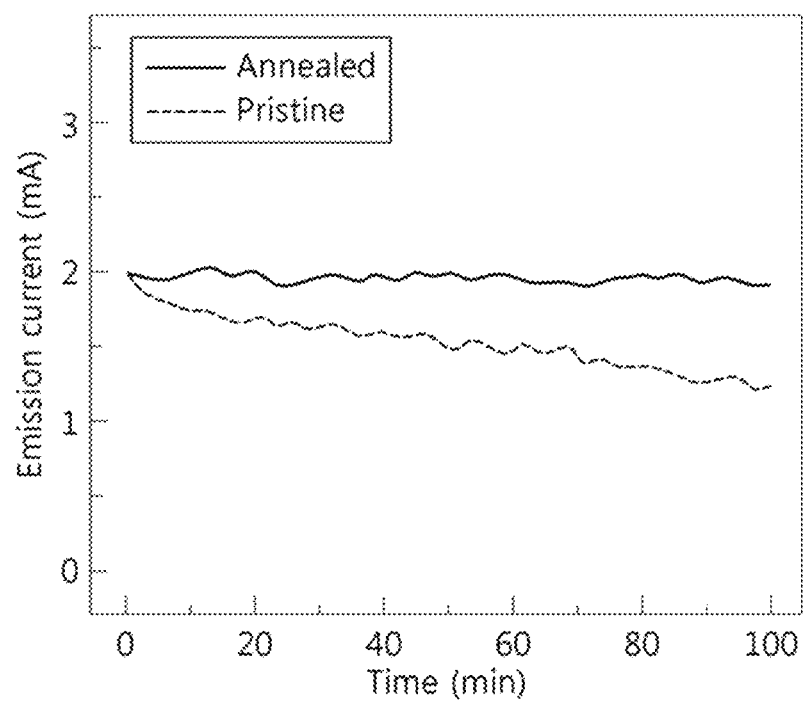

FIELD EMISSION-TYPE TOMOSYNTHESIS SYSTEM, EMITTER FOR FIELD EMISSION-TYPE TOMOSYNTHESIS SYSTEM, AND METHOD OF MANUFACTURING EMITTER

CROSS-REFERENCE TO RELATED APPLICATIONS

This application is a National Stage Entry of PCT International Application No. PCT/KR2019/016427, which was filed on Nov. 27, 2019, and claims priority to Korean Patent Application No. 10-2018-0149004, filed on Nov. 27, 2018, and Korean Patent Application No. 10-2018-0148994, filed on Nov. 27, 2018, in the Korean Intellectual Property Office, the disclosures of each of which are incorporated herein by reference.

TECHNICAL FIELD

The present invention relates to a field emission-type tomosynthesis system, an emitter for the field emission-type tomosynthesis system, and a method of manufacturing the emitter. More particularly, the present invention relates to a field emission-type tomosynthesis system capable of creating a 3D image from a photographed image by emitting and focusing a plurality of X-rays on an object; an emitter for the field emission-type tomosynthesis system; and a method of manufacturing the emitter.

BACKGROUND ART

In general, an X-ray tube is a vacuum tube for generating X-rays. The cathode of an X-ray tube is formed of tungsten filaments and emits thermal electrons when heated by current. When a high voltage of tens of thousands of volts or more is applied to the anode of the X-ray tube, electron flow emitted from the cathode moves toward the anode at high speed. At this time, when the electron flow collides with a counter electrode made of tungsten, molybdenum, etc., which is the anode, energy is emitted as X-rays.

Observing human tissues using radiological approaches has advantages such as non-invasiveness, and thus has provided great benefits to humans. In addition, due to radiological approaches in biotechnology and medicine, it is possible to observe tissues ranging in size from several millimeters to several micrometers, which greatly improves research and development activities and human health.

However, conventional radiation apparatuses having micrometer-scale resolution have difficulty in observing microstructures due to lack of spatial resolving power. Accordingly, when observing a microstructure, a huge particle accelerator is required. In addition, since conventional micro X-ray apparatuses use a filament-based electron emission source, the dose (flux) of emission X-rays is insufficient, and thus the conventional micro X-ray apparatuses have a limitation in being applied to various imaging apparatuses.

Accordingly, in recent years, various research for obtaining high-resolution X-ray images is continuously being conducted.

DISCLOSURE

Technical Problem

Therefore, the present invention has been made in view of the above problems, and it is one object of the present invention to provide a field emission-type tomosynthesis system capable of increasing resolution through information synthesis by focusing a plurality of X-rays on an object.

It is another object of the present invention to provide an emitter for a field emission-type tomosynthesis system, characterized in that pattern formation is easy.

It is still another object of the present invention to provide an emitter for a field emission-type tomosynthesis system, characterized in that holes form a pattern on a substrate without a lithography process.

It is still another object of the present invention to provide an emitter for a field emission-type tomosynthesis system, characterized in that there is no interference due to different carbon nanotubes when the carbon nanotubes emit electrons, and capable of emitting a large number of electrons even at a low voltage.

It is yet another object of the present invention to provide an emitter for a field emission-type tomosynthesis system, characterized in that a pattern formation process is simple compared to a silicon substrate.

Technical Solution

In accordance with one aspect of the present invention, provided is a field emission-type tomosynthesis system including a vacuum body having a space therein; a plurality of sources provided inside the body, wherein each of the sources generates and emits a plurality of electrons; and anodes arranged to face the sources inside the body, wherein the electrons collide with each of the anodes to generate a plurality of X-rays, wherein an X-ray emission angle of each of the anodes is capable of being independently adjusted so as to focus the X-rays emitted toward an object located outside the body.

In addition, each of the sources may include carbon nanotubes (CNTs) and generate the electrons, and information of the object photographed by the X-rays is capable of being synthesized by a computer.

In addition, the sources may be provided in plural and may be arranged in a row so as to be placed side by side with each other, and the anodes may be disposed to correspond to the sources and may be arranged in a row so as to be placed side by side with each other.

In addition, the sources and the anodes may each number between 5 to 100.

In addition, each of the anodes may have a reflective surface where the electrons collide, and the anodes may be rotated while being supported by the body, so that angles of each of the reflective surfaces are adjustable.

In addition, the sources may be simultaneously supported by source supports and are fixed to the body through a source fixture, and the anodes may be simultaneously supported by an anode support and are fixed to the body through an anode fixture.

In addition, each of the anodes may be rotatably supported by the anode support, so that X-ray reflection angles of each of the anodes are independently adjusted.

In accordance with another aspect of the present invention, provided is a field emission-type tomosynthesis system including a plurality of sources for generating electrons; and a plurality of anodes responsible for emitting X-rays and disposed to face the sources, wherein each of the anodes has a reflective surface where the electrons collide, X-rays are emitted from the reflective surfaces as a result of collision of the electrons, and each of the anodes faces a corresponding source among the sources, wherein each angle of the reflective surfaces is independently adjustable so that the X-rays emitted from each of the anodes are directed at one point.

In addition, the sources and the anodes may be provided inside a body having a space therein, and may emit the X-rays through an emission hole formed through the body.

In addition, each of the sources may include carbon nanotubes (CNTs) and may generate the electrons, and information obtained by focusing the X-rays on an object to be photographed and emitting the X-rays to the object may be synthesized using a computer.

In addition, the sources may be provided in plural and may be arranged in a row so as to be placed side by side with each other, the anodes may be disposed to correspond to the sources and may be arranged in a row so as to be placed side by side with each other, and the sources and the anodes may each number between 5 to 100.

In addition, each of the anodes may be rotatably supported by an anode support, so that angles of reflective surfaces of each of the anodes are independently adjusted.

In accordance with still another aspect of the present invention, provided are an emitter for a field emission-type tomosynthesis system and a method of manufacturing the emitter, wherein the emitter with improved field emission performance is manufactured by growing carbon nanotubes on a pattern formed on a metal substrate and performing heat treatment, and the method includes a step of preparing a substrate; a step of forming a pattern by forming a plurality of holes through perforation in the substrate; a step of growing carbon nanotubes (CNTs) on the substrate on which the pattern has been formed by the holes; and a step of heat-treating the CNTs grown on the substrate at high temperature.

Preferably, according to the present invention, a width of the holes formed in the substrate may be at least twice a height of the CNTs grown on the substrate.

Preferably, according to the present invention, the holes may be formed in a size of 10 to 60 µm through perforation when the pattern is formed, and a height of the CNTs grown on the substrate may be 1 to 30 µm.

Preferably, according to the present invention, the step of growing CNTs on the substrate may include a step of cleaning the substrate using isopropyl alcohol, and then cleaning the substrate using deionized water; a step of placing the substrate in a chamber, and performing control so that an inside of the chamber is in a vacuum state; a step of heating the chamber to a temperature of 600° C. to 1,000° C. at a rate of 20° C./min in a vacuum state; and a step of performing a pretreatment process of reducing an oxidized layer on a surface of the substrate by supplying ammonia ($NH_3$) gas to the chamber at a flow rate of 10 to 70 sccm (standard cubic centimeter per minute) for 5 to 50 minutes and maintaining internal pressure at 200 mTorr to 20 Torr.

Preferably, according to the present invention, the method may include a step of supplying, to the pretreated substrate in the chamber, acetylene ($C_2H_2$) at a flow rate of 5 to 70 sccm and ammonia ($NH_3$) gas at a flow rate of 5 to 70 sccm for 30 minutes and maintaining internal pressure at 1 mTorr to 20 Torr; and a step of cooling the chamber to room temperature when CNTs are grown on the substrate.

Preferably, according to the present invention, in the step of heating the CNTs-grown substrate at high temperature, the substrate is placed in the chamber, and is heat-treated at a temperature of 600° C. to 2,500° C. for 15 minutes in a vacuum state, thereby improving crystallinity of the CNTs, reducing defects of the CNTs, and improving field emission performance.

Preferably, according to the present invention, the pattern formed on the substrate may be formed by alternately arranging pads and holes on one surface of the substrate, and may include at least one of a stripe shape, a polygonal shape, and a circular shape.

Preferably, according to the present invention, the holes may be formed through a laser etching process or a wet etching process.

Preferably, according to the present invention, the substrate may be formed of a metal alloy material including at least one metal of nickel, iron, chromium, and cobalt.

In accordance with yet another aspect of the present invention, provided is an emitter for a field emission-type tomosynthesis system including a substrate formed of a metal material and having a pattern formed by a plurality of holes formed on one surface thereof; and carbon nanotubes (CNTs) grown on the substrate, wherein a width of the holes formed in the substrate is at least twice a height of the CNTs grown on the substrate.

Preferably, according to the present invention, the holes may be formed in a size of 10 to 600 µm through perforation when the pattern is formed on the substrate, and a height of the CNTs grown on the substrate may be 5 to 100 µm.

Preferably, according to the present invention, the holes may be formed in a surface of the substrate through a laser etching process or a wet etching process.

Preferably, according to the present invention, the substrate may be formed of a metal alloy material including at least one metal of nickel, iron, chromium, and cobalt.

Advantageous Effects

According to the present invention having the configuration as described above, first, each of a plurality of sources emits electrons, and each of a plurality of anodes emits the electrons, so that a plurality of X-rays can be focused on one object. Accordingly, leakage can be minimized while emitting an electric field such as X-rays.

Second, high-resolution 3D image information can be obtained by synthesizing information captured by a plurality of X-rays focused on an object.

Third, diseases that are difficult to diagnose early, such as lung cancer, can be diagnosed early through high-resolution X-ray imaging.

Fourth, an emitter for a field emission-type tomosynthesis system according to the present invention has the effect of simplifying a process of forming holes in a surface.

Fifth, in the emitter for a field emission-type tomosynthesis system according to the present invention, since holes are formed in a pattern, interference of carbon nanotubes emitting electrons can be prevented.

Sixth, in the emitter for a field emission-type tomosynthesis system according to the present invention, the crystallinity of CNT is improved and defects are reduced through a high-temperature heat treatment process. Accordingly, field emission performance can be improved.

Seventh, in the emitter for a field emission-type tomosynthesis system according to the present invention, even when a low voltage is applied, a large number of electrons can be emitted.

DESCRIPTION OF DRAWINGS

FIG. 1 is a perspective view schematically showing a field emission-type tomosynthesis system according to a preferred embodiment of the present invention.

FIG. 2 is a side view schematically showing a state in which the field emission-type tomosynthesis system shown in FIG. 1 faces an object.

FIG. 3 is an exploded perspective view schematically showing the interior of the field emission-type tomosynthesis system 1 shown in FIG. 1.

FIG. 4 is an enlarged perspective view schematically showing one of a plurality of sources of the field emission-type tomosynthesis system shown in FIG. 3.

FIG. 5 is a top view schematically showing a state in which the gate electrodes and the focusers of the source shown in FIG. 3 are separated from each other.

FIG. 6 is an enlarged top view schematically showing the VI region shown in FIG. 5.

FIG. 7 schematically illustrates a plurality of anodes of the field emission-type tomosynthesis system shown in FIG. 3.

FIG. 8 illustrates the sources and the anodes shown in FIG. 3 facing each other as viewed from the side where the anodes are located.

FIG. 9 is a perspective view schematically showing the anode shown in FIG. 7.

FIG. 10 illustrates an emitter for a field emission-type tomosynthesis system according to the present invention.

FIGS. 11A and 11B illustrate an emitter for a field emission-type tomosynthesis system according to the present invention and a flat emitter, respectively.

FIGS. 12 to 14 are graphs for comparing the performance of an emitter for a field emission-type tomosynthesis system according to the present invention and a flat emitter.

FIGS. 15 and 16 are flowcharts for explaining a process of manufacturing an emitter for a field emission-type tomosynthesis system according to the present invention.

FIGS. 17A to 17D include a drawing and an image for explaining a heat treatment process of an emitter for a field emission-type tomosynthesis system according to the present invention, and enlarged images of carbon nanotubes (CNTs) before and after heat treatment.

FIG. 18 is a graph showing Raman analysis performed before and after heat treatment of an emitter for a field emission-type tomosynthesis system according to the present invention.

FIGS. 19 and 20 are graphs for comparing performance before and after heat treatment of an emitter for a field emission-type tomosynthesis system according to the present invention.

BEST MODE

Hereinafter, preferred embodiments of the present invention will be described with reference to the accompanying drawings. However, the spirit of the present invention is not limited to the embodiments, and the spirit of the present invention may be proposed differently by adding, changing, and deleting the elements constituting the embodiments, which is also within the spirit of the present invention.

Referring to FIGS. 1 to 3, a field emission-type tomosynthesis system 1 according to a preferred embodiment of the present invention includes a body 10, sources 20, and anodes 30.

FIG. 1 is a perspective view schematically showing the field emission-type tomosynthesis system 1 according to a preferred embodiment of the present invention, FIG. 2 is a side view schematically showing a state in which the field emission-type tomosynthesis system 1 shown in FIG. 1 faces an object (O), and FIG. 3 is an exploded perspective view schematically showing the interior of the field emission-type tomosynthesis system 1 shown in FIG. 1.

As shown in FIGS. 1 and 2, a space is formed inside the body 10, and the body 10 is a kind of vacuum tube. The inside of the body 10 is provided with the sources 20 and the anodes 30 to be described later, and the body 10 surrounds, supports, and protects the sources 20 and the anodes 30. In addition, the body 10 has an approximately rectangular parallelepiped shape, and an emission hole 11 opened toward the object (O) is formed through one side thereof. X-rays (X), which are electromagnetic waves, are emitted to the object (O) through the emission hole 11.

For reference, since the body 10 is formed of a non-metallic material such as ceramic and glass, i.e., an insulating material, electrical interference with electrons (E) generated from the sources 20 to be described later may be effectively prevented.

The sources 20 are provided inside the body 10, and generate the electrons (E) (see FIG. 3) for field emission. As shown in FIG. 3, the sources 20 are provided in plural, are arranged in a row so as to be placed side by side with each other, and are supported by the inside of the body 10. More specifically, as shown in FIG. 4, the sources 20 are arranged in a row so as to be placed side by side with each other, and are supported by source supports 21. In addition, the source supports 21 are fixed to a source fixture 22 while supporting the sources 20, and are fixed inside the body 10.

In addition, in the present embodiment, the sources 20 are provided in in plural and are arranged in a row so as to be placed side by side with each other, but the present invention is not limited thereto. That is, the sources 20 may be disposed in multiple rows, or may be disposed adjacent to each other in the circumferential direction.

As shown in FIG. 3, the source supports 21 have a rectangular plate shape extending in the longitudinal direction to support the arrangement of the sources 20 in a line, and are fixed to the source fixture 22. In addition, the source fixture 22 has a plate shape corresponding to the source supports 21 and is coupled to the source supports 21. In addition, the source fixture 22 is fixed to the body 10 by coupling source fixing protrusions 22a inside of the body 10. By the source supports 21 and the source fixture 22, the sources 20 are fixed inside of the body 10 so as to be arranged in a row and be placed side by side with each other.

In addition, as shown in FIG. 4, each of the sources 20 includes a cathode substrate electrode 23, an emitter 24, a gate electrode 25, and a focuser 28, and generates the electrons (E). The cathode substrate electrode 23, the emitter 24, the gate electrode 25, and the focuser 28 are laminated, and are fixed to the source supports 21 via connectors 27. Here, the emitter 24 is not shown in detail, but may include carbon nanotubes (CNTs) and may generate the electrons (E).

In addition, as shown in FIG. 5, the gate electrodes 25 are provided in plural and supported by a first source support 21a. The focusers 28 are provided in plural and supported by a second source support 21b. In this case, the gate electrodes 25 supported by the first source support 21a face the emitters 24, and the focusers 28 supported by the second source support 21b are laminated on the first source support 21a to face the gate electrodes 25.

As shown in FIGS. 4 and 6, holes 26 through which the electrons (E) generated from the emitter 24 pass are formed in the center of each of the gate electrodes 25. A mesh 26 for extracting the electrons (E) is provided in the holes 26. In addition, the focusers 28 are laminated to face the gate electrodes 25, respectively, and a focusing hole 29 is formed through the center of each of the focusers 28. With this configuration, the generated electrons (E) are focused so that the generated electrons (E) are not spread or scattered and move toward the anode 30.

In addition, the source 20 including the cathode substrate electrode 23, the emitter 24 including carbon nanotubes (CNTs), the gate electrode 25, and the focuser 28 may include an electron emitter or an electron gun for emitting the electrons (E) for generating X-rays (X). The configuration of the cathode substrate electrode 23, the emitter 24, the gate electrode 25, and the focuser 28 included in the source 20 may be understood from a known technique for emitting X-rays, and thus a detailed description thereof will be omitted since it is not the gist of the present invention.

As shown in FIG. 3, the anodes 30 are provided in plural and are arranged to face the sources 20, respectively. In addition, the anodes 30 are placed side by side with each other. In the present embodiment, corresponding to the configuration of the sources 20 arranged in a row to be adjacent to each other, the anodes 30 are provided in plural and are arranged in a row to be adjacent to each other. However, the configuration of the anodes 30 is not limited thereto, and as in the case of the sources 20, the anodes 30 may be disposed in multiple rows, or may be disposed adjacent to each other in the circumferential direction.

For reference, in this embodiment, approximately 85 sources 20 are provided and are arranged in a row to be adjacent to each other, and approximately 85 anodes 30 are provided and are arranged in a row to be adjacent to each other. However, the number of the sources 20 and the anodes 30 may be adjusted as necessary between approximately 5 to 100.

Each of the anodes 30 is provided with a reflective surface 30*a* (see FIG. 9) for reflecting the electrons (E) after collision. With this configuration, the electrons (E) emitted from the sources 20 collide with the anodes 30, and generate the X-rays (X), which are electromagnetic waves, to emit the X-rays (X) to the object (O) provided outside the body 10.

That is, the field emission-type tomosynthesis system 1 according to the present invention may include an X-ray imaging device capable of obtaining a desired image by emitting the X-rays (X) to the object (O). However, the present invention is not limited thereto, and the sources 20 and the anodes 30 may be employed as any one of various electromagnetic wave source systems for emitting electromagnetic waves other than the X-rays (X).

In addition, as shown in FIG. 7, the anodes 30 are placed on an anode support 31 having an approximately rectangular plate shape so as to be arranged in a row and placed side by side with each other, and the anodes 30 are supported by the anode support 31. The anode support 31 is fixed to the inside of the body 10 via an anode fixture 32 while supporting the anodes 30. The anode support 31 and the anode fixture 32 may be formed of materials and may have properties similar to those of the source supports 21 and the source fixture 22 described above.

In addition, as shown in FIGS. 7 and 8, each of the anodes 30 is arranged to be inclined and is supported by the anode support 31, so that the angle of each of the reflective surfaces 30*a* facing the object (O) may be adjusted. As shown in FIGS. 8 and 9, each of the anodes 30 is provided with an anode protrusion 33 and is supported by the anode support 31. In this case, the anode protrusion 33 has a cylindrical shape and is connected to the anode support 31, so that the anode 30 rotates in the R direction as shown in FIG. 9 around the anode protrusion 33, and the angle of each of the reflective surfaces 30*a* is adjusted.

Each of the anodes 30 is rotated in the R direction around the anode protrusion 33 while being supported by the anode support 31, so that the angle of each of the reflective surfaces 30*a* is adjusted. Thus, when the electrons (E) generated from the sources 20 collide with each of the reflective surfaces 30*a* and are emitted as the X-rays (X), the angle of reflection of each of the reflective surfaces 30*a* may be adjusted. The posture of the anodes 30 may be manually adjusted by an operator or may be adjusted by electronic control. In addition, the inclination angle of the anodes 30 is not limited to the illustrated example, and may be variously changed according to the location, size, and distance of the object (O).

In addition, as shown FIG. 2, the object (O) includes a detector facing the field emission-type tomosynthesis system 1, and the detector is disposed so that a patient (H) to be photographed is located between the detector and the field emission-type tomosynthesis system 1. In this case, the anodes 30 may emit the X-rays (X) to the object (O) in the form of a cone, i.e., a V-beam shape. The X-rays (X) emitted in a V-beam shape cover the entire area of the object (O), which is the detector. Accordingly, as shown in FIG. 3, regardless of the area and size of the object (O), the X-rays (X) may be focused on the center of the object (O).

In addition, the angle of inclination of the reflective surface 30*a* of each of the anodes 30 is adjusted to emit the X-rays (X) vertically with respect to the center of the object (O). Accordingly, as shown in FIG. 7, the angle of each of the reflective surfaces 30*a* is adjusted so that the angle of each of the anodes 30 disposed at both sides of the anode 30 facing the center of the object (O) among the anodes 30 arranged in a row is adjusted to be inclined toward the center of the object (O), i.e., the detector. For reference, the angle of the anodes 30 is not limited to the example of FIG. 7, and may be adjusted according to the location of the object (O).

An X-ray emitting operation of the field emission-type tomosynthesis system 1 according to the present invention having such a configuration will be described with reference to FIGS. 2 and 3.

As shown in FIG. 2, the field emission-type tomosynthesis system 1 is disposed to face the object (O). As shown in FIG. 3, the electrons (E) are generated from the sources 20 arranged in a row. The generated electrons (E) collide with the reflective surfaces 30*a* of the anodes 30 facing the sources 20, and the electrons (E) are converted into the X-rays (X). The X-rays (X) generated from the anodes 30 in this way each have different reflection angles due to the inclined installation angles of each of the anodes 30. Thus, as shown in FIGS. 3 and 7, the anodes 30 emit the reflected X-rays (X) toward the object (O) and focus the X-rays (X) on a point of the object (O).

Information of the object (O) is photographed by the X-rays (X) emitted to the object (O). The information photographed by the X-rays (X) is synthesized by a computer to obtain high-resolution 3D image information of the object (O).

FIG. 10 illustrates an emitter for a field emission-type tomosynthesis system according to the present invention.

A patterned carbon nanotube emitter 110 (hereinafter referred to as a substrate) according to the present invention is formed of a metal material, and a plurality of holes 114 formed through one surface thereof forms a pattern. The emitter 110 includes CNTs 120 grown thereon. Pads 112 on which the CNTs 120 are formed and the holes 114 may be alternately arranged to form a stripe pattern. For example, the length (1) of each of the pads 112 on which the CNTs 120 are formed may be 0.04 mm, and the length (d) of each of the holes 114 may be 0.15 mm, but the present invention is not limited thereto.

The holes 114 are formed on one surface of the emitter 110, and the CNTs 120 are grown on the pads 112. Since the emitter 110 is formed of a metal material, pattern formation may be easy compared to conventional silicon substrates.

The holes 114 formed on one surface of the emitter 110 may have various shapes. In addition to a stripe shape, the holes 114 may be formed in at least one of polygonal and circular shapes, and the holes 114 are preferably formed to have a stripe shape. The holes 114 may be formed using laser etching using a high frequency of a laser such as an excimer laser or a YAG laser, or wet etching in which a part of a surface is corroded using a chemical such as an inorganic acid.

The CNTs 120 emit electrons in a field emission method, and are formed on the top of the pads 112. The CNTs 120 may be formed in an irregular shape toward the upper side of the pad 112. The CNTs 120 may be grown using plasma enhanced chemical vapor deposition (PECVD), characterized in that supplying hydrocarbon gas, or thermal chemical vapor deposition (thermal CVD). The specific growth method of the CNTs 120 will be described in detail below.

FIGS. 11A and 11B show an emitter 110 for a field emission-type tomosynthesis system according to the present invention and a flat emitter 130, respectively.

The emitter 110 is formed of an alloy material including at least one of nickel (Ni), iron (Fe), chromium (Cr), and cobalt (Co) or other metals, and the holes 114 are formed in one surface of the emitter 110, and a stripe pattern is formed on the emitter 110.

In addition, when the CNTs 120 are grown on the flat emitter 130 on which a pattern is not formed, the CNTs 120 grow unevenly in the form of spaghetti over the entire area of the flat emitter 130. When the flat emitter 130 is used as an electron emission source, the non-uniformly grown CNTs 120 block electrons emitted from the neighboring CNTs 120, thus reducing electron emission efficiency.

However, when the emitter 110 according to the present invention is used as an electron emission source, since the CNTs 120 located on the pads 112 formed at regular intervals are relatively less susceptible to interference by other CNTs 120 duet to spaced spaces formed by the holes 114, when the same voltage is supplied, the quantity of electrons emitted from the emitter 110 according to the present invention is much larger than the quantity of electrons emitted from the flat emitter 130.

Preferably, when a distance (d) of the holes 114 formed in the emitter 110 is 10 to 60 μm, and a height (h) of the CNTs 120 grown on the emitter 110 is 1 to 30 μm, a large number of electrons may be emitted from the emitter 110. Most preferably, the distance (d) of the holes 114 formed in the emitter 110 is at least twice the height (h) of the CNTs 120 grown on the emitter 110. That is, the pattern of the emitter 110 should be formed and the CNTs 120 should be grown to meet the condition of d>2 h.

FIGS. 12 to 14 are graphs showing the performance of an emitter for a field emission-type tomosynthesis system according to the present invention and the performance of a flat emitter.

It can be seen that, when a voltage of 1,200 V is supplied to the emitter 110 on which a pattern has been formed by the holes 114, and a voltage of 1,800 V is supplied to the flat emitter 130 without holes, the magnitude of cathode current over time is higher in the emitter 110. It can be seen that, even when a voltage supplied to the flat emitter 130 without holes is about 600 V higher than a voltage supplied to the emitter 110, compared to the flat emitter 130 without holes, the emitter 110 on which a pattern has been formed by the holes 114 maintains higher cathode current over time.

In addition, it can be seen that, as gate current increases, the cathode current of the emitter 110 on which a pattern has been formed by the holes 114 is higher than the cathode current of the flat emitter 130 without holes. As a gate current value increases, the cathode current of the emitter 110 on which a pattern has been formed by the holes 114 is significantly increased. In addition, when comparing current density according to gate current, the current density of the emitter 110 on which a pattern has been formed by the holes 114 is higher than the current density of the flat emitter 130 without holes.

Referring to the graphs, it can be seen that the quantity of electrons emitted from the emitter 110 on which a pattern has been formed by the holes 114 is larger than the quantity of electrons emitted from the flat emitter 130 without holes. Accordingly, even when a voltage applied to the emitter 110 on which a pattern has been formed by the holes 114 is less than a voltage applied to the flat emitter 130 without holes, the quantity of electrons emitted from the emitter 110 is larger than the quantity of electrons emitted from the flat emitter 130. Accordingly, when the emitter 110 having a pattern is applied to an X-ray tube, economic feasibility and efficiency may be improved.

FIGS. 15 and 16 are flowcharts for explaining a process of manufacturing an emitter for a field emission-type tomosynthesis system according to the present invention.

The manufacturing process of the emitter 110 includes step S10 of preparing a substrate, step S20 of forming a pattern by forming a plurality of holes through perforation in the substrate, step S30 of forming CNTs on the substrate on which the pattern has been formed by the holes, and step S40 of heat-treating the CNTs grown on the substrate at high temperature.

In step S10 of preparing a substrate, the emitter 110 is formed of a stainless steel alloy, or may be formed of another metal or an alloy of another material. The emitter 110 may have a rectangular shape and an emitter 110 having rounded corners may be used. Alternatively, the emitter 110 may have a polygonal shape such as a square or a circular shape. The emitter 110 is preferably formed of a metal material that facilitates the growth of the CNTs 120, and the emitter 110 having an appropriate size to be introduced into the chamber 140 is preferably used.

In step S20 of forming a pattern by forming a plurality of holes in the substrate, the holes 114 formed in the emitter 110 are formed by forming the holes 114 through perforation in one surface of the emitter 110, and as a result of forming the holes 114, a stripe shape is formed. The holes 114 formed in one surface of the emitter 110 are formed through a laser etching process or a wet etching process. In the pattern, the pads 112 on which the CNTs 120 are located and the spaces penetrating the emitter 110 are arranged in a lattice structure.

In step S30 of forming CNTs on the substrate on which the pattern has been formed by the holes, the CNTs 120 are grown on the pads 112 formed on the emitter 110. Before growing the CNTs 120, by preheating the surface of the emitter 110, the growth of the CNTs 120 may be promoted.

The process of preheating may include step S31 of cleaning the substrate using isopropyl alcohol, and then cleaning the substrate using deionized water, step S32 of placing the substrate, and performing control so that the inside of the chamber is in a vacuum state, step S33 of heating the chamber to a temperature of 600° C. to 1,000°

C. at a rate of 20° C./min in a vacuum state, and step S34 of supplying ammonia ($NH_3$) gas to the chamber at a flow rate of 10 to 70 sccm (standard cubic centimeter per minute) for 5 to 50 minutes and maintaining internal pressure at 200 mTorr to 20 Torr. Since the oxidized layer of the surface of the preheated-emitter 110 is reduced, the growth of the CNTs 120 may be promoted.

To grow the CNTs 120 on the substrate that has been preheated, step S35 of supplying acetylene ($C_2H_2$) and ammonia ($NH_3$) gas to the chamber at a flow rate of 5 to 70 sccm for 30 minutes while the substrate being placed in the chamber, and maintaining internal pressure at 1 mTorr to 20 Torr; and step S36 of cooling the chamber to room temperature when the CNTs are grown on the pattern are performed.

In step S35 of growing the CNTs by supplying gas to the substrate, the CNTs 120 grow in an irregular shape on the pads 112 of the emitter 110, and the grown CNTs 120 have a thickness of 50 to 100 nm and a length of about 5 μm.

Through step S36 of cooling the chamber to room temperature, the emitter 110 may be used as an electron emission source. The emitter 110 on which the CNTs 120 have been grown may be used as an electron emission source, but through step S40 of heat-treating the CNTs grown on the substrate at high temperature, electron emission performance may be improved. The process of heat treatment will be described below.

FIGS. 17A to 17D show a heat treatment process of an emitter for a field emission-type tomosynthesis system according to the present invention and show enlarged images of CNTs before and after heat treatment.

When the CNTs 120 have sufficiently grown on the emitter 110, the emitter 110 may be used as an electron emission source. However, when the emitter 110 is subjected to a heat treatment process once more at preset temperature and pressure, the performance of the emitter 110 may be further improved.

In step S40 of heat-treating the CNTs grown on the substrate at high temperature, the emitter 110 on which the CNTs 120 have been grown is placed in a chamber 140, a vacuum atmosphere is formed, and the CNTs 120 are grown by heating at the same or higher temperature for a preset time without separate gas supply. Preferably, the emitter 110 on which the CNTs 120 have been grown is placed in the chamber 140, and heat treatment is performed at a temperature of 600° C. to 2,500° C. for 15 minutes in a vacuum state.

Comparing an image (c) and an image (d), the image (c) shows the appearance of the CNTs 120 before heat treatment, and the image (d) shows the appearance of the CNTs 120 after heat treatment. In this case, the crystallinity of the CNTs 120 of the image (d) is improved, and the defects of the CNTs 120 of the image (d) are reduced.

FIG. 18 is a graph showing Raman analysis performed before and after heat treatment of an emitter for a field emission-type tomosynthesis system according to the present invention, and FIGS. 19 and 20 are graphs for comparing performance before and after heat treatment of the emitter for a field emission-type tomosynthesis system according to the present invention.

Referring to a graph obtained by analyzing the substrate 110 (Pristine) before heat treatment and the substrate 110 (Annealed) after heat treatment by Raman spectroscopy, two vertices are formed in the graph. The first vertex (D) represents the degree to which the CNTs 120 are irregularly formed (disorder defect). As the height of the vertex (D) increases, the irregularity of the CNT 120 increases, resulting in poor crystallinity. Since the position of the vertex of the substrate 110 (Annealed) after heat treatment is lower than the position of the vertex of the substrate 110 (Pristine) before heat treatment, compared to the emitter 110 before heat treatment, the substrate 110 (Annealed) after heat treatment has relatively few defects that are associated with irregularities. That is, since CNTs having defects are removed by the heat treatment process, the crystallinity of the CNTs 120 may be increased.

In addition, the second vertex (G) represents the crystallinity of the CNTs 120. As the second vertex (G) value increases, crystallinity increases. That is, the position of the vertex of the emitter 110 after heat treatment is higher than the position of the vertex of the emitter 110 before heat treatment, indicating that the crystallinity of the substrate 110 (Annealed) after heat treatment is high.

For more accurate comparison, when the same voltage is applied to the emitter 110 before heat treatment and the emitter 110 after heat treatment, the performance thereof may be compared through a graph.

When an electric field is supplied to the substrate 110 (Pristine) before heat treatment and the substrate 110 (Annealed) after heat treatment, the quantity of emission current generated from the emitter 110 after heat treatment is greater than the quantity of emission current generated from the emitter 110 before heat treatment.

Another graph shows emission current over time. The emitter 110 after heat treatment shows little change in emission current over time. On the other hand, in the emitter 110 before heat treatment, emission current gradually decreases over time.

That is, based on these results, when the emitter 110 after heat treatment rather than the emitter 110 before heat treatment is applied to an X-ray tube, field emission performance may be further improved.

Although the present invention has been described above with reference to the embodiments of the present invention, those skilled in the art may variously modify and change the present invention without departing from the spirit and scope of the present invention as set forth in the claims below.

The invention claimed is:

1. A field emission-type tomosynthesis system; comprising:
    a vacuum body having a space therein;
    a plurality of sources provided inside the body, wherein each of the plurality of sources generates and emits a plurality of electrons;
    a source support having a rectangular plate extending in a vertical direction to support the plurality of sources;
    a plurality of anodes arranged to face the plurality of sources inside the body, wherein the electrons collide with the plurality of anodes to generate a plurality of X-rays; and
    an anode support having a rectangular plate extending in the vertical direction to support the plurality of anodes,
    wherein the plurality of anodes have a plurality of protrusions each of which extends in a horizontal direction,
    wherein the rectangular plate of the anode support incudes a plurality of holes through which the plurality of protrusions pass,
    wherein each anode of the plurality of anodes includes a reflective surface and a protrusion extending the horizontal direction, and
    wherein each anode of the plurality of anodes is rotatable around a protrusion formed in the each anode of the plurality of anodes and passing through the rectangular plate of the anode support to adjust an X-ray emission angle of each of the plurality of anodes independently so as to focus the X-rays emitted toward an object located outside the body.

2. The X-ray source system according to claim 1, wherein each of the sources comprises carbon nanotubes (CNTs) and generates the electrons, and
information of the object photographed by the X-rays is capable of being synthesized.

3. The field emission-type tomosynthesis system according to claim 1, wherein the sources are arranged in a row so as to be placed side by side with each other, and
the anodes are disposed to correspond to the sources and are arranged in a row so as to be placed side by side with each other.

4. The field emission-type tomosynthesis system according to claim 1, wherein the sources and the anodes each number between 5 to 100.

5. The field emission-type tomosynthesis system according to claim 1, wherein the sources are simultaneously supported by the source support and are fixed to the body through a source fixture, and
the anodes are simultaneously supported by the anode support and are fixed to the body through an anode fixture.

6. The field emission-type tomosynthesis system according to claim 5, wherein each of the anodes is rotatably supported by the anode support, so that an X-ray reflection angle of each of the anodes is independently adjusted.

7. A field emission-type tomosynthesis system; comprising:
a plurality of sources for generating electrons;
a source support having a rectangular plate extending in a vertical direction to support the plurality of sources;
a plurality of anodes for emitting X-rays and disposed to face the plurality of sources; and
an anode support having a rectangular plate extending in the vertical direction to support the plurality of anodes,
wherein the plurality of anodes have a plurality of protrusions each of which extends in a horizontal direction,
wherein the rectangular plate of the anode support incudes a plurality of holes through which the plurality of protrusions pass,
wherein each of the plurality of anodes has a reflective surface where the electrons collide, X-rays are emitted from reflective surfaces of the plurality of anodes as a result of collision of the electrons, and each of the plurality of anodes faces a corresponding source among the plurality of sources, and
wherein each anode of the plurality of anodes is rotatable around a protrusion formed in the each anode of the plurality of anodes and passing through the rectangular plate of the anode support to adjust each angle of the reflective surfaces is independently so that the X-rays emitted from each of the plurality of anodes are directed at one point.

8. The field emission-type tomosynthesis system according to claim 7, wherein the sources and the anodes are provided inside a vacuum body having a space therein, and emit the X-rays through an emission hole formed through the body.

9. The X-ray source system according to claim 7, wherein each of the sources comprises carbon nanotubes (CNTs) and generates the electrons, and
information obtained by focusing the X-rays on an object to be photographed and emitting the X-rays to the object is capable of being synthesized using a computer.

10. The field emission-type tomosynthesis system according to claim 7, wherein the sources are arranged in a row so as to be placed side by side with each other,
the anodes are disposed to correspond to the sources and are arranged in a row so as to be placed side by side with each other, and
the sources and the anodes each number between 5 to 100.

11. The field emission-type tomosynthesis system according to claim 7, wherein each of the anodes is rotatably supported by the anode support, so that an angle of a reflective surface of each of the anodes is independently adjusted.

12. A method of manufacturing an emitter for a field emission-type tomosynthesis system, wherein the field emission-type tomosynthesis system comprises a plurality of sources provided inside a vacuum body having a space therein and responsible for emitting electrons, and the method comprises a step of preparing a substrate;
a step of forming a pattern by forming a plurality of holes through perforation in the substrate;
a step of growing carbon nanotubes (CNTs) on the substrate on which the pattern has been formed by the holes; and
a step of heat-treating the CNTs grown on the substrate at high temperature.

13. The method according to claim 12, wherein a width of the holes formed in the substrate is at least twice a height of the CNTs grown on the substrate.

14. The method according to claim 12, wherein the holes are formed in a size of 10 to 60 μm through perforation when the pattern is formed, and a height of the CNTs grown on the substrate is 1 to 30 μm.

15. The method according to claim 12, wherein the step of growing CNTs on the substrate comprises a step of cleaning the substrate using isopropyl alcohol, and then cleaning the substrate using deionized water;
a step of placing the substrate in a chamber, and performing control so that an inside of the chamber is in a vacuum state;
a step of heating the chamber to a temperature of 600° C. to 1,000° C. at a rate of 20° C./min in a vacuum state; and
a step of performing a pretreatment process of reducing an oxidized layer on a surface of the substrate by supplying ammonia (NH3) gas to the chamber at a flow rate of 10 to 70 sccm (standard cubic centimeter per minute) for 5 to 50 minutes and maintaining internal pressure at 200 mTorr to 20 Torr.

16. The method according to claim 15, comprising:
a step of supplying, to the pretreated substrate in the chamber, acetylene (C2H2) at a flow rate of 5 to 70 sccm and ammonia (NH3) gas at a flow rate of 5 to 70 sccm for 30 minutes and maintaining internal pressure at 1 mTorr to 20 Torr; and
a step of cooling the chamber to room temperature when CNTs are grown on the substrate.

17. The method according to claim 12, wherein, in the step of heating the CNTs-grown substrate at high temperature, the substrate is placed in the chamber, and is heat-treated at a temperature of 600° C. to 2,500° C. for 15 minutes in a vacuum state, thereby improving crystallinity of the CNTs, reducing defects of the CNTs, and improving field emission performance.

18. The method according to claim 12, wherein the pattern formed on the substrate is formed by alternately arranging pads and holes on one surface of the substrate, and comprises at least one of a stripe shape, a polygonal shape, and a circular shape.

19. The method according to claim 18, wherein the holes are formed through a laser etching process or a wet etching process.

\* \* \* \* \*